United States Patent
Burbar et al.

(10) Patent No.: US 12,329,557 B2
(45) Date of Patent: Jun. 17, 2025

(54) FEEDBACK COOLING SYSTEM FOR AN IMAGING SYSTEM

(71) Applicant: Siemens Medical Solutions USA, Inc., Malvern, PA (US)

(72) Inventors: Ziad Burbar, Knoxville, TN (US); John Keller, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 65 days.

(21) Appl. No.: 18/262,755

(22) PCT Filed: Jun. 30, 2021

(86) PCT No.: PCT/US2021/070792
§ 371 (c)(1),
(2) Date: Jul. 25, 2023

(87) PCT Pub. No.: WO2023/277954
PCT Pub. Date: Jan. 5, 2023

(65) Prior Publication Data
US 2024/0407743 A1    Dec. 12, 2024

(51) Int. Cl.
*A61B 6/00* (2024.01)
*A61B 6/03* (2006.01)

(52) U.S. Cl.
CPC ............ *A61B 6/4488* (2013.01); *A61B 6/037* (2013.01)

(58) Field of Classification Search
CPC ............ A61B 6/448; A61B 6/037; A61B 6/03
See application file for complete search history.

(56) References Cited

U.S. PATENT DOCUMENTS

| | | |
|---|---|---|
| 2006/0215808 A1 | 9/2006 | Lacey et al. |
| 2017/0176607 A1 | 6/2017 | Liu et al. |
| 2017/0192067 A1 * | 7/2017 | Garcia ................... A61B 5/055 |

FOREIGN PATENT DOCUMENTS

| | | | | |
|---|---|---|---|---|
| DE | 102017131317 A1 * | 7/2018 | ........... | A47K 10/423 |
| WO | WO-2009150576 A1 * | 12/2009 | ......... | G01R 33/3804 |

OTHER PUBLICATIONS

International Search Report for Corresponding PCT Application No. PCT/US2021/07092, mailed Mar. 21, 2022.

* cited by examiner

*Primary Examiner* — Emmanuel E Duke

(57) ABSTRACT

A cooling system for cooling a component of an imaging system located in a scan room. The system includes inlet, outlet and return channels. A portion of warm outlet air from a component outlet flows in the return channel to provide warm recirculated air to a mixing zone in the inlet channel. A fan located in the inlet channel draws scan room air into the inlet channel to mix with the warm recirculated air in the mixing zone to form mixed air that flows over the component to cool the component and wherein the mixed air absorbs heat that warms the mixed air to form the warm outlet air. A valve located in the return channel restricts or allows additional warm recirculated air to flow to the mixing zone to mix with the scan room air to maintain a desired control temperature for the cooling system.

20 Claims, 5 Drawing Sheets

FEEDBACK COOLING SYSTEM FOR AN IMAGING SYSTEM

TECHNICAL FIELD

Aspects of the present invention relate to a cooling system for an imaging system, and more particularly, to a cooling system for cooling at least one component of the imaging system wherein the cooling system uses a portion of warm air from an outlet of the component that is then recirculated and mixed with scan room air to provide air within a narrow temperature range that flows at a high air flow rate to cool the component.

BACKGROUND

Many medical imaging systems, such as positron emission tomography/computed tomography (PET/CT) imaging systems, are cooled by a cooling media such as liquid, air or a combination of liquid and air. With respect to air cooled imaging systems, it is desirable that the ambient air temperature in a scan room at a customer site wherein the imaging system operates be within a required operating temperature range for proper operation of the imaging system. The room temperature range required for proper operation of the imaging system is frequently too narrow for the needs of the customer site. Some customer sites have a room temperature that is lower than the required lower temperature limit for proper operation of the imaging system whereas other sites have a room temperature that is above the required upper limit for proper operation of the imaging system. When the room temperature is outside of the operating temperature range of the imaging system, warning and error indications are generated by the imaging system which may cause the imaging system to undesirably shut down.

Referring to FIG. 1, an exemplary conventional air cooling system 10 for cooling a component 12 of an imaging system is shown. The cooling system 10 includes inlet 14 and outlet 16 conduits and a fan 18 located in the inlet conduit 14. The cooling system 10 also includes a controller 20 that regulates a fan speed of the fan 18 in response to scan room ambient and component temperatures detected by scan room 22 and component 24 temperature sensors, respectively. In use, cooling air at atmospheric pressure is drawn through an air filter 26 and into the inlet conduit 14 by the fan 18 and flows through a low pressure zone 28 located before the fan 18. The air then flows over the component 12 and dissipates heat from the component 12 thus cooling the component 12 and warming the air. Warm air at a relatively high pressure then exits from the outlet conduit 16.

The conventional method to cooling has been to drive air in an open loop by controlling fan speed which changes the air flow rate through the cooling system 10. In this method, fan speed is reduced when the scan room is relatively cold and then increased as the scan room temperature rises. Further, internal imaging system temperatures change with room temperature. When fan speed decreases, the internal imaging system temperature increases and when fan speed increases, the internal imaging system temperatures decrease. The cooling system 10 is driven by the ambient air room temperature and the heat load generated by the imaging system which may result in the exposure of internal imaging system components to a wide range of temperatures. For example, the range of controlled temperatures is normally set at a relatively wide temperature range (24-38° C., or 15° C. for example) since this is a function of the ambient air temperature (18-30° C., for example) and the heat being dissipated in the imaging system. However, the cooling system 10 may not be able to maintain the temperature of the components being cooled in their operating or targeted range when the ambient air room temperature goes outside specified limits. Further, in components such as silicon photomultipliers (SiPM) detectors used in PET/CT imaging systems, a temperature compensation circuit having a detector compensation algorithm is utilized to correct for temperature variability in the detector. However, the targeted temperature range (i.e., the range of controlled temperatures) can vary by more than 15° C., for example. With such a range, the detector compensation algorithm becomes more difficult to characterize.

SUMMARY OF THE INVENTION

A cooling system for cooling at least one component of an imaging system located in a scan room is disclosed. The system includes inlet and outlet channels in air flow communication with the component and a return channel in air flow communication with the inlet and outlet channels, wherein a portion of warm outlet air from a component outlet flows in the return channel to provide warm recirculated air to a mixing zone in the inlet channel. The system also includes a fan located in the inlet channel that draws scan room air into the inlet channel wherein the room air is mixed with the warm recirculated air in the mixing zone to form mixed air that flows over the component to cool the component and wherein the mixed air absorbs heat that warms the mixed air to form the warm outlet air. Further the system includes a valve located in the return channel, wherein the valve restricts or allows additional warm recirculated air to flow through the return channel to the mixing zone to mix with the scan room air to maintain a desired control temperature for the cooling system.

Those skilled in the art may apply the respective features of the present invention jointly or severally in any combination or sub-combination.

BRIEF DESCRIPTION OF THE DRAWINGS

The exemplary embodiments of the invention are further described in the following detailed description in conjunction with the accompanying drawings, in which.

DETAILED DESCRIPTION

Figure 1:
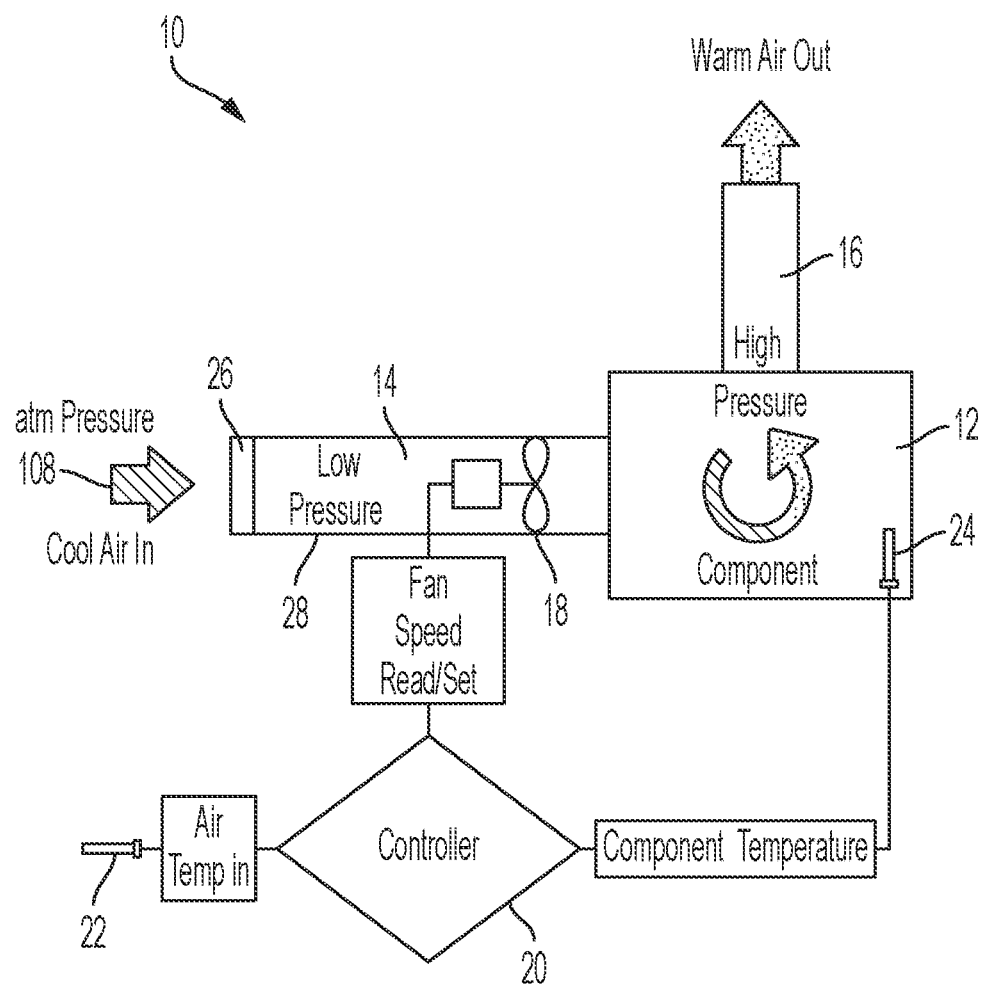
FIG. 1 shows an exemplary conventional air cooling system for cooling a component of an imaging system.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Figure 2:
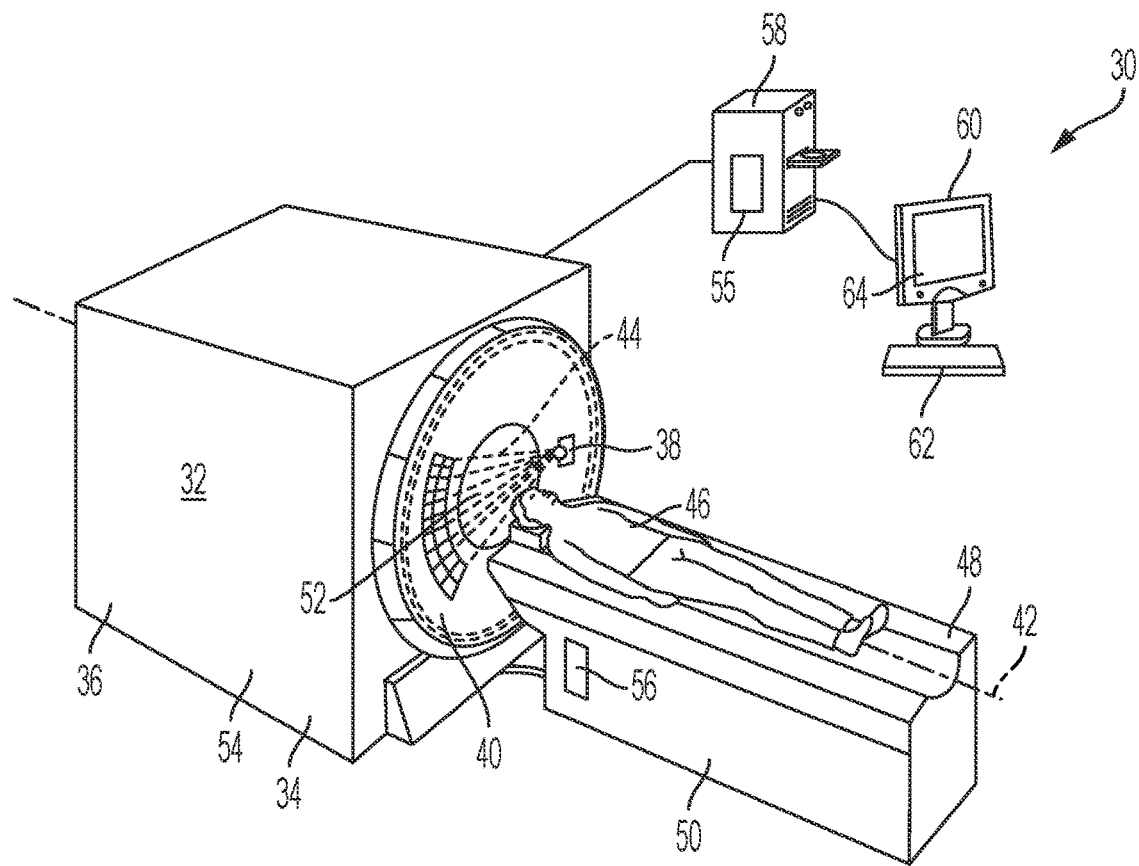
FIG. 2 is a perspective view of an exemplary medical imaging system that utilizes the invention.

Referring to FIG. 2, a perspective view of an exemplary medical imaging system 30 in accordance with an aspect of the invention is shown. The invention may be used in conjunction with a positron emission tomography/computed tomography (PET/CT) imaging system 32 having a CT portion 34 and a PET portion 36 although it is understood that the invention may be used in other types of imaging systems. The CT portion 34 includes a recording unit, comprising an X-ray source 38 and an X-ray detector 40. The recording unit rotates about a longitudinal axis 42 during the recording of a tomographic image, and the X-ray source 38 emits X-rays 44 during a spiral recording. While an image is being recorded a patient 46 lies on a moveable bed 48 located on a table base 50. The bed 48 is designed to move the patient 46 along a recording direction through an opening or tunnel 52 of a gantry 54 of the imaging system 32. The table base 50 includes a control unit 56 connected to a computer 58 to exchange data. The computer 58 includes a determination unit 55 in the form of a computer program that can be executed on the computer 58. The computer 58 is connected to an output unit 60 and an input unit 62. The output unit 60 is, for example, one (or more) liquid crystal display (LCD) or plasma screen(s). An output 64 on the output unit 60 comprises, for example, a graphical user interface for actuating the individual units of the imaging system 32 and the control unit 56. The input unit 62 is for example a keyboard, mouse, touch screen or a microphone for speech input.

Figure 3:
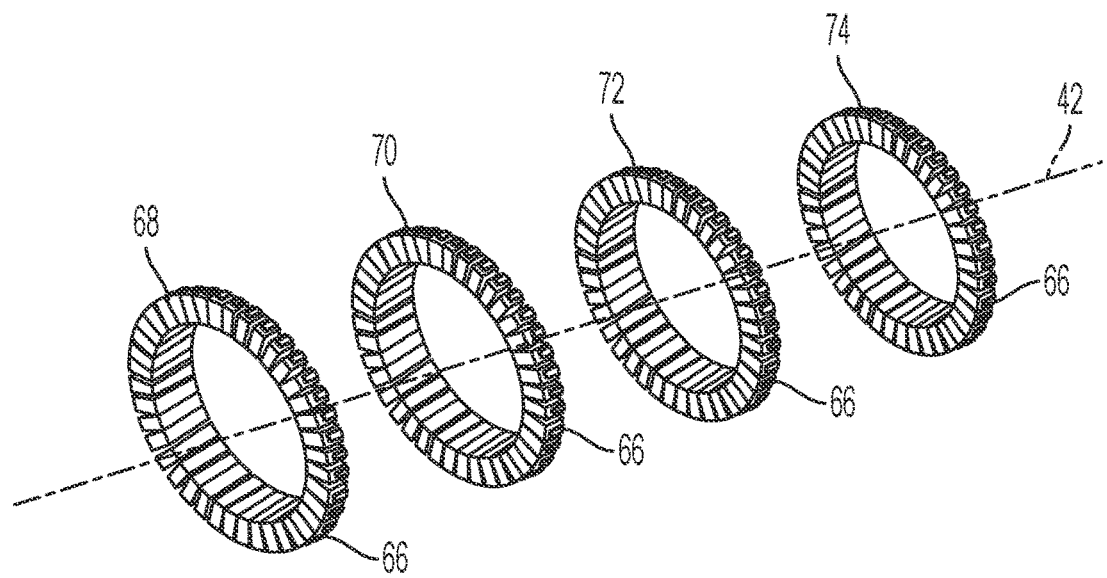
FIG. 3 depicts a plurality of PET detector rings of a PET portion of the medical imaging system.

Referring to FIG. 3, the PET portion 36 includes a plurality of PET detector rings 66 arranged about the longitudinal axis 42. For purposes of illustration, exemplary first 68, second 70, third 72 and fourth 74 detector rings are shown. Each detector ring 68, 70, 72, 74 includes a plurality of PET detectors 66 used to scan the patient 46 located in the tunnel 52. During a known operation of the PET portion 36 of imaging system 32, a patient 46 located in the tunnel 52 is injected with a radioisotope. The radioisotope undergoes positron emission decay and emits a positron that encounters and annihilates with an electron to produce a pair of gamma rays moving in approximately opposite directions. The gamma rays are detected by the PET detectors 66 and information from the gamma rays is used to generate PET images. The PET images are then used in conjunction with CT images generated by the CT portion 34 of imaging system 32 to provide images of the patient 46 or part of a patient's anatomy. Each PET detector 66 generates heat during operation of the PET portion 36.

Figure 4:
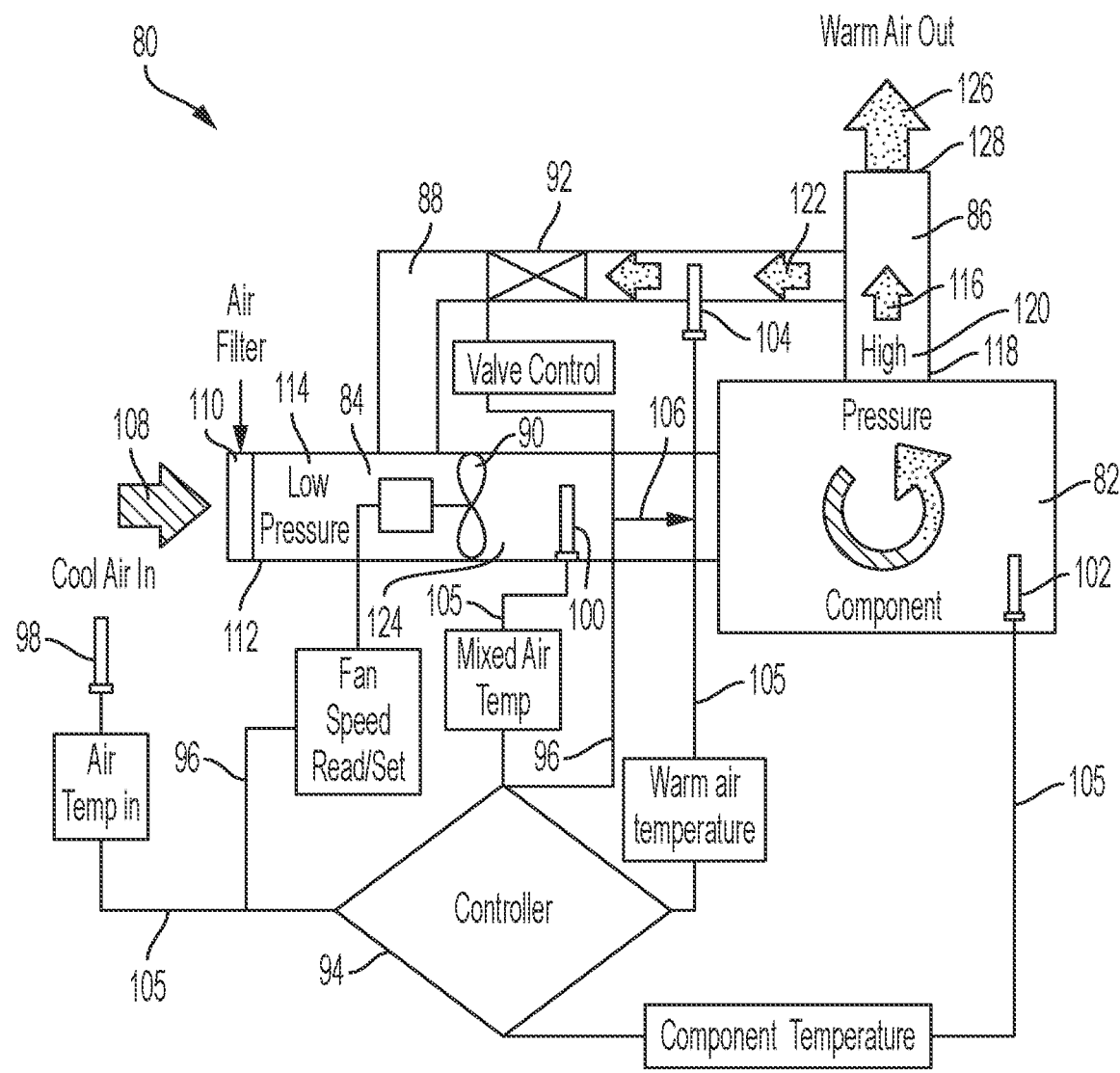
FIG. 4 shows an embodiment of a feedback air cooling system for cooling a component of the imaging system.

Referring to FIG. 4, an embodiment of a feedback air cooling system 80 for cooling at least one component 82 of an imaging system 30 is shown. By way of example, the imaging system 30 may be the PET/CT imaging system 32 and the component 82 may be a PET detector 66 although it is understood that other types of imaging systems and associated components are within the scope of the invention. In accordance with an aspect of the invention, a cooling fluid such as air is used to cool the component although a liquid, or combination of liquid and air, may be used. For purposes of illustration, the invention will be described in connection with a PET/CT imaging system 32 that uses air as a cooling fluid.

The cooling system 80 includes inlet 84 and outlet 86 channels that are in air flow communication with the component 82 to be cooled and a return channel 88 that is in air flow communication with the outlet 86 and inlet 84 channels. The cooling system 80 also includes at least one variable speed fan 90 and at least one valve 92 that are each connected to a controller 94 by respective control lines 96. In an embodiment, the fan 90 is located in the inlet channel 84 and the valve 92 is located in the return channel 88. In other embodiments, the fan 90 and valve 92 may be located in other suitable positions in the cooling system 80 in addition to or instead of the inlet 84 and return 88 channels. The cooling system 80 further includes first 98, second 100, third 102 and fourth 104 temperature sensors located in the scan room, the inlet channel 84, on the component 82 and in the return channel 88, respectively, that provide temperature data to the controller via respective signal lines 105 connected between the first 98, second 100, third 102 and fourth 104 temperature sensors and the controller 94. The valve 92 is an electronically actuated valve controlled by the controller 94 to partially open as desired. In an embodiment, the valve 92 may be an electronically actuated butterfly valve. The controller 94 also controls a fan speed of the fan 90 to provide a desired flow of mixed air 106 to the component 82.

In operation, the fan 90 draws in scan room ambient air 108 at atmospheric pressure through a filter 110 located on an inlet end 112 of the inlet channel 84. The room air 108 then flows through a low pressure zone 114 formed before the fan 90 and subsequently past the fan 90 and the component 82 to dissipate heat from the component 82. This cools the component 82 and forms warm outlet air 116 that exits a component outlet 118 at high pressure 120. When the valve 92 is partially opened, a portion of warm outlet air 116 from the component outlet 118 flows through the return channel 88 to provide warm recirculated air 122 to an air mixing zone 124 in the inlet channel 84. In the mixing zone 124, the warm recirculated air 122 is mixed with the room air 108 by the fan 90 to form mixed air 106 that subsequently flows past the component 82 to cool the component 82 and forms the warm outlet air 116. A remaining portion of the warm outlet air 106 that does not flow into the return channel 88 (i.e., exhaust air 126) exits an outlet end 128 of the outlet channel 86.

The mixing of warm recirculated air 122 with room air 108 provides mixed air 106 that is warmer than the room air 108. The second temperature sensor 100 is positioned in the inlet channel 84 after the mixing zone 124 to provide mixed air temperature data to the controller 94. The controller 94 may vary a valve opening of the valve 92 to restrict or allow additional warm recirculated air 122 into the return channel 88 and subsequently the mixing zone 124 based on the detected mixed air temperature provided by the second temperature sensor 100 in order to maintain a desired target or control temperature. The controller 94 may also adjust a fan speed of the fan 90 in order to maintain the control temperature and/or provide a desired air flow rate. In accordance with an embodiment of the invention, this provides a range of control temperatures for the mixed air 106 that is sufficient for cooling the component 82 and narrower than in conventional cooling systems. In addition, a control temperature of the cooling system can be set at a higher temperature to enable higher air flow into the cooling system.

Figure 5A:
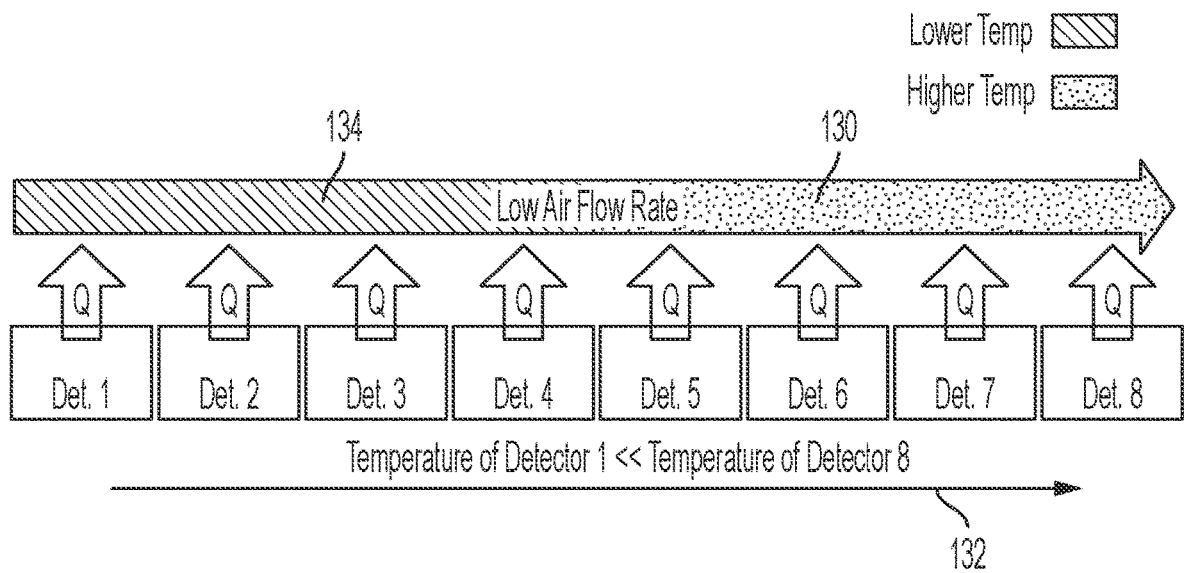
FIG. 5A is a schematic representation of a temperature gradient of exemplary PET detectors 1-8 of an imaging system having eight PET detector rings wherein the PET detectors are cooled by air flowing at a low air flow rate.

It has been found that when the air speed of scan room air flowing across PET detectors is low, an undesirable temperature gradient develops across the PET detectors in an axial direction substantially parallel to the longitudinal axis 42. FIG. 5A is a schematic representation of a temperature gradient 130 in an axial direction 132 substantially parallel to the longitudinal axis 42 (FIG. 3) for exemplary PET detectors 1-8 (referenced as Det. 1-Det. 8) in a PET portion 36 (FIG. 2) having eight PET detector rings. Each PET detector 1-8 generates heat during operation of the PET portions 36. An amount of heat Q is transferred from each PET detector 1-8 to cooling air (depicted by arrow 134) flowing at a relatively low air flow rate in the axial direction 132. When using a relatively low air flow rate, the temperature of PET detector 1 is much less than that of PET detector 8, for example, thus forming a relatively large temperature difference between the first PET detector (PET detector 1) and last PET detector (PET detector 8).

Figure 5B:
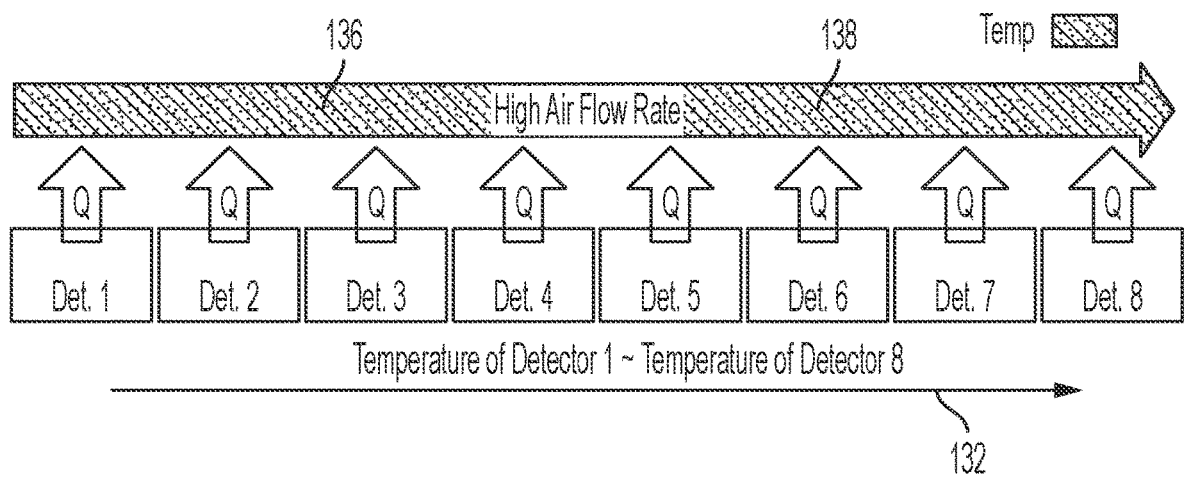
FIG. 5B is a schematic representation of a temperature gradient of exemplary PET detectors 1-8 of an imaging system having eight PET detector rings wherein the PET detectors are cooled by air flowing at a higher air flow rate.

FIG. 5B is a schematic representation of a temperature gradient 136 in the axial direction 132 when the cooling air 138 flows at a higher air flow rate. When this occurs, the amount of heat Q transferred from each PET detector 1-8 to cooling air 138 flowing at a higher air flow rate is greater than that transferred at the lower air flow rate. This results in the temperature of PET detector 1 (the first PET detector) being much closer to that of PET detector 8 (the last PET detector), for example. In accordance with an aspect of the invention, the temperature difference between the PET detector 1 and PET detector 8 in the axial series is minimized by keeping the mixed air temperature 106 in a narrow range and the air flow rate high.

The invention may be used in PET systems having a long axial field of view (FoV), for example, an axial FoV of more than approximately 30 cm, wherein a higher air flow across the PET detectors lowers the temperature gradient across the PET detectors in the axial direction 132, as shown in FIG. 5B. Additionally, the invention may be used in PET systems having a relatively short axial FoV (for example, a FoV of less than approximately 30 cm). In particular, a PET system having a short axial FoV may not provide sufficient heat dissipation to satisfy a lower temperature boundary and a slowest fan speed. The current invention enables additional air flow (i.e., a higher flow rate) in a short axial FoV system when the ambient air room temperature is low by opening the valve 92 to mix additional warm outlet air 116 into the cooling system 80. In accordance with an aspect of the invention, the range of the control temperatures can be set to a narrower range than conventional cooling systems. In an embodiment, the range of control temperatures is approximately 32-36° C.

Figure 6A:
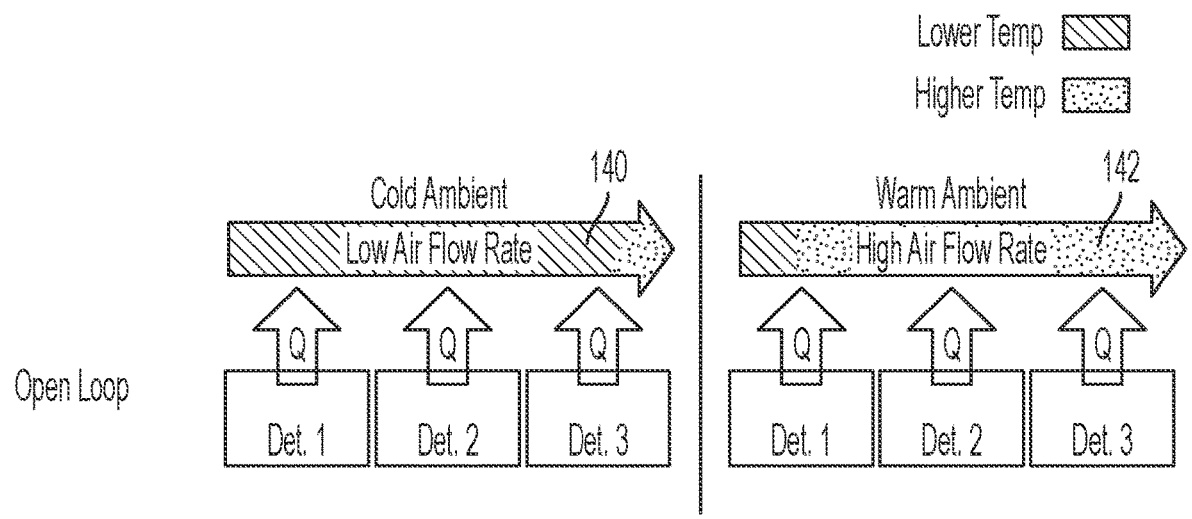
FIG. 6A is a schematic representation of temperature gradients for a PET portion having a short axial field of view (FoV) when using a conventional cooling system (i.e., open loop system) under cold and warm ambient conditions.

FIG. 6A is a schematic representation of temperature gradients for a PET portion 36 having a short axial FoV when using the conventional cooling system 10 (i.e., open loop system) under cold and warm ambient conditions. The PET portion 36 includes exemplary PET detectors 1-3 (referenced as Det. 1-Det. 3) having three PET detector rings that form a short axial FoV system. A temperature gradient 140 under cold ambient temperature conditions and a low air flow rate indicates that the amount of heat transferred Q from each PET detectors 1-3 is less than the amount of heat transferred Q under warm ambient temperature conditions and a high air flow rate as indicated by temperature gradient 142.

Figure 6B:
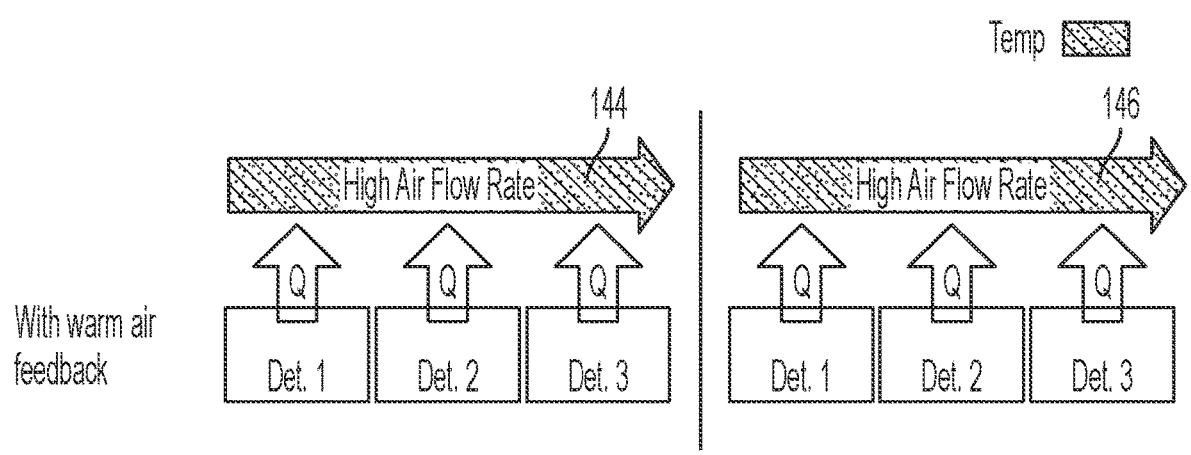
FIG. 6B is a schematic representation of temperature gradients for a PET portion having a short axial FoV when using the cooling system of the invention (i.e., warm air feedback) under cold and warm ambient conditions.

FIG. 6B is a schematic representation of temperature gradients for a PET portion 36 having a short axial FoV when using the cooling system 80 of the invention (i.e., warm air feedback) under cold and warm ambient conditions. In particular, FIG. 6B shows that a temperature gradient 144 under cold ambient temperature conditions and a low air flow rate is substantially similar to a temperature gradient 146 under warm ambient temperature conditions and a high air flow rate.

In addition to the advantages described above, the invention enables the use of a simplified detector compensation algorithms for the SiPM detectors used in PET/CT imaging systems. Further, the invention avoids the use of inline heaters to warm inlet air flow which would increase cost and power usage and undesirably increase the carbon footprint of an imaging system.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A cooling system for cooling at least one component of an imaging system located in a scan room, comprising:
   inlet and outlet channels in air flow communication with the component;
   a return channel in air flow communication with the inlet and outlet channels, wherein a portion of warm outlet air from a component outlet flows in the return channel to provide warm recirculated air to a mixing zone in the inlet channel; and
   a fan located in the inlet channel, wherein the fan draws scan room air into the inlet channel and wherein the scan room air is mixed with the warm recirculated air in the mixing zone to form mixed air wherein the mixed air flows over the component to cool the component and wherein the mixed air absorbs heat that warms the mixed air to form the warm outlet air.

2. The cooling system in accordance with claim 1, further including a valve located in the return channel, wherein the valve restricts or allows additional warm recirculated air to flow through the return channel to the mixing zone to mix with the scan room air.

3. The cooling system according to claim 2, wherein the valve is a butterfly valve.

4. The cooling system according to claim 3, further including a temperature sensor coupled to a controller, wherein the temperature sensor is located in the inlet channel to detect a mixed air temperature wherein the controller controls the valve to restrict or allow additional warm recirculated air based on the mixed air temperature to maintain a desired control temperature.

5. The cooling system according to claim 4, wherein the warm recirculated air mixed with scan room air enables a higher control temperature to enable higher air flow into the cooling system.

6. The cooling system in accordance with claim 4, wherein restricting or allowing additional warm recirculated air forms a narrow range of control temperatures.

7. The cooling system according to claim 1, wherein the mixed air used to cool the component flows at a high air flow rate to minimize a temperature difference between components oriented along an axis of the imaging system.

8. The cooling system according to claim 7, wherein the imaging system has a short axial field of view and the high air flow rate is maintained when the scan room air temperature is low.

9. A cooling system for cooling at least one component of an imaging system located in a scan room, comprising:
   inlet and outlet channels in air flow communication with the component;
   a return channel in air flow communication with the inlet and outlet channels, wherein a portion of warm outlet air from a component outlet flows in the return channel to provide warm recirculated air to a mixing zone in the inlet channel;
   a fan located in the inlet channel, wherein the fan draws scan room air into the inlet channel and wherein the scan room air is mixed with the warm recirculated air in the mixing zone to form mixed air wherein the mixed air flows over the component to cool the component and wherein the mixed air absorbs heat that warms the mixed air to form the warm outlet air; and
   a valve located in the return channel, wherein the valve restricts or allows additional warm recirculated air to flow through the return channel to the mixing zone to mix with the scan room air to maintain a desired control temperature for the cooling system.

10. The cooling system according to claim 9, wherein the valve is a butterfly valve.

11. The cooling system according to claim 9, further including a temperature sensor coupled to a controller, wherein the temperature sensor is located in the inlet channel to detect a mixed air temperature wherein the controller controls the valve to restrict or allow additional recirculated air based on the mixed air temperature to maintain the control temperature.

12. The cooling system according to claim 9, wherein the warm recirculated air mixed with scan room air enables a higher control temperature to enable higher air flow into the cooling system.

13. The cooling system in accordance with claim 9, wherein restricting or allowing additional warm recirculated air forms a narrow range of control temperatures.

14. The cooling system according to claim 9, wherein the warm outlet air used to cool the component flows at a high air flow rate to minimize a temperature difference between components oriented along an axis of the imaging system.

15. The cooling system according to claim 14, wherein the imaging system has a short axial field of view and the high air flow rate is maintained when the scan room air temperature is low.

16. The cooling system according to claim 9, wherein the imaging system is a positron emission tomography/computed tomography (PET/CT) imaging system.

17. The cooling system according to claim 16, wherein the at least one component is a PET detector.

18. A method of cooling at least one component of an imaging system located in a scan room, comprising:
   providing inlet and outlet air passageways to enable air flow into and out of the component;
   providing a return air passageway to enable a portion of warm outlet air from the component to flow in the return air passageway to provide warm recirculated air to a mixing zone in the inlet air passageway;
   drawing scan room air into the inlet air passageway;
   mixing the scan room air with the warm recirculated air in the mixing zone to form mixed air wherein the mixed air flows over the component to cool the component and wherein the mixed air absorbs heat that warms the mixed air to form the warm outlet air.

19. The method of cooling according to claim 18, further including restricting or allowing additional warm recirculated air to flow through the return air passageway to the mixing zone to mix with the scan room air.

20. The method of cooling according to claim 19, further including detecting a mixed air temperature wherein the controller controls the valve to restrict or allow additional warm recirculated air based on the mixed air temperature to maintain a desired control temperature.

* * * * *